(12) United States Patent
Quinn

(10) Patent No.: US 6,942,653 B2
(45) Date of Patent: *Sep. 13, 2005

(54) BLOOD VESSEL CATHETER

(75) Inventor: David G. Quinn, Grayslake, IL (US)

(73) Assignee: Radius International Limited Partnership, Grayslake, IL (US)

( * ) Notice: Subject to any disclaimer, the term of this patent is extended or adjusted under 35 U.S.C. 154(b) by 89 days.

This patent is subject to a terminal disclaimer.

(21) Appl. No.: 09/853,916

(22) Filed: May 11, 2001

(65) Prior Publication Data

US 2002/0169457 A1 Nov. 14, 2002

(51) Int. Cl.$^7$ ............................................. A61M 25/00
(52) U.S. Cl. ...................................................... 604/523
(58) Field of Search ........................ 604/270, 43, 264, 604/523, 541, 170.01, 170.03, 524

(56) References Cited

U.S. PATENT DOCUMENTS

| | | | |
|---|---|---|---|
| 1,879,249 A | | 9/1932 | Honsaker |
| 2,116,083 A | * | 5/1938 | Rusch ........................ 604/523 |
| 3,384,089 A | | 5/1968 | Shriner |
| 3,589,368 A | | 6/1971 | Jackson et al. |
| 4,037,599 A | | 7/1977 | Raulerson |
| 4,134,402 A | | 1/1979 | Mahurkar |
| 4,270,542 A | | 6/1981 | Plumley |
| 4,311,140 A | | 1/1982 | Bridgman |
| 4,368,737 A | | 1/1983 | Ash |
| 4,381,011 A | | 4/1983 | Somers, 3rd |
| 4,445,897 A | | 5/1984 | Ekbladh et al. |
| 4,498,902 A | | 2/1985 | Ash et al. |
| 4,529,399 A | | 7/1985 | Groshong et al. |
| 4,549,879 A | | 10/1985 | Groshong et al. |
| 4,559,039 A | | 12/1985 | Ash et al. |
| 4,568,329 A | | 2/1986 | Mahurkar |
| 4,583,968 A | | 4/1986 | Mahurkar |
| 4,623,327 A | | 11/1986 | Mahurkar |
| 4,639,252 A | | 1/1987 | Kelly et al. |
| 4,671,796 A | | 6/1987 | Groshong et al. |
| 4,692,141 A | | 9/1987 | Mahurkar |
| 4,692,153 A | | 9/1987 | Berlin et al. |
| 4,701,166 A | | 10/1987 | Groshong et al. |
| 4,770,652 A | | 9/1988 | Mahurkar |
| 4,772,266 A | | 9/1988 | Groshong |
| 4,781,678 A | | 11/1988 | de Couët et al. |
| 4,808,155 A | | 2/1989 | Mahurkar |
| 4,842,582 A | | 6/1989 | Mahurkar |
| 4,895,561 A | | 1/1990 | Mahurkar |
| 4,898,669 A | | 2/1990 | Tesio |
| 5,053,004 A | | 10/1991 | Markel et al. |
| 5,197,951 A | | 3/1993 | Mahurkar |
| 5,221,255 A | | 6/1993 | Mahurkar et al. |
| 5,221,256 A | * | 6/1993 | Mahurkar ..................... 604/43 |
| 5,269,770 A | * | 12/1993 | Conway et al. ........ 604/101.05 |
| 5,322,519 A | | 6/1994 | Ash |
| 5,336,177 A | | 8/1994 | Marcus |
| 5,374,245 A | | 12/1994 | Mahurkar |
| 5,378,230 A | | 1/1995 | Mahurkar |
| 5,451,216 A | | 9/1995 | Quinn |
| 5,486,159 A | | 1/1996 | Mahurkar |
| 5,571,093 A | * | 11/1996 | Cruz et al. ................... 604/264 |
| 5,599,322 A | * | 2/1997 | Quinn ........................ 604/270 |
| 5,607,405 A | | 3/1997 | Decker et al. |
| 5,624,413 A | | 4/1997 | Markel et al. |
| 5,685,836 A | | 11/1997 | DiPerna et al. |
| 5,776,111 A | | 7/1998 | Tesio |
| 5,947,953 A | | 9/1999 | Ash et al. |
| 5,984,913 A | | 11/1999 | Kritzinger et al. |
| 6,511,474 B1 | * | 1/2003 | Andersen ..................... 604/264 |
| 2002/0026156 A1 | * | 2/2002 | Quinn ........................ 604/264 |

* cited by examiner

Primary Examiner—Nicholas D. Lucchesi
Assistant Examiner—Matthew F DeSanto
(74) Attorney, Agent, or Firm—Brinks Hofer Gilson & Lione

(57) ABSTRACT

A blood vessel catheter including a catheter tube and a bolus having a bullet nose. The bolus includes a passage section with a side opening port. A nose section with a bullet nose has a smaller cross-section than the rest of the bolus and is offset from the axis of the passage section in the radial direction of the port. The bullet nose is rounded and unperforated.

15 Claims, 2 Drawing Sheets

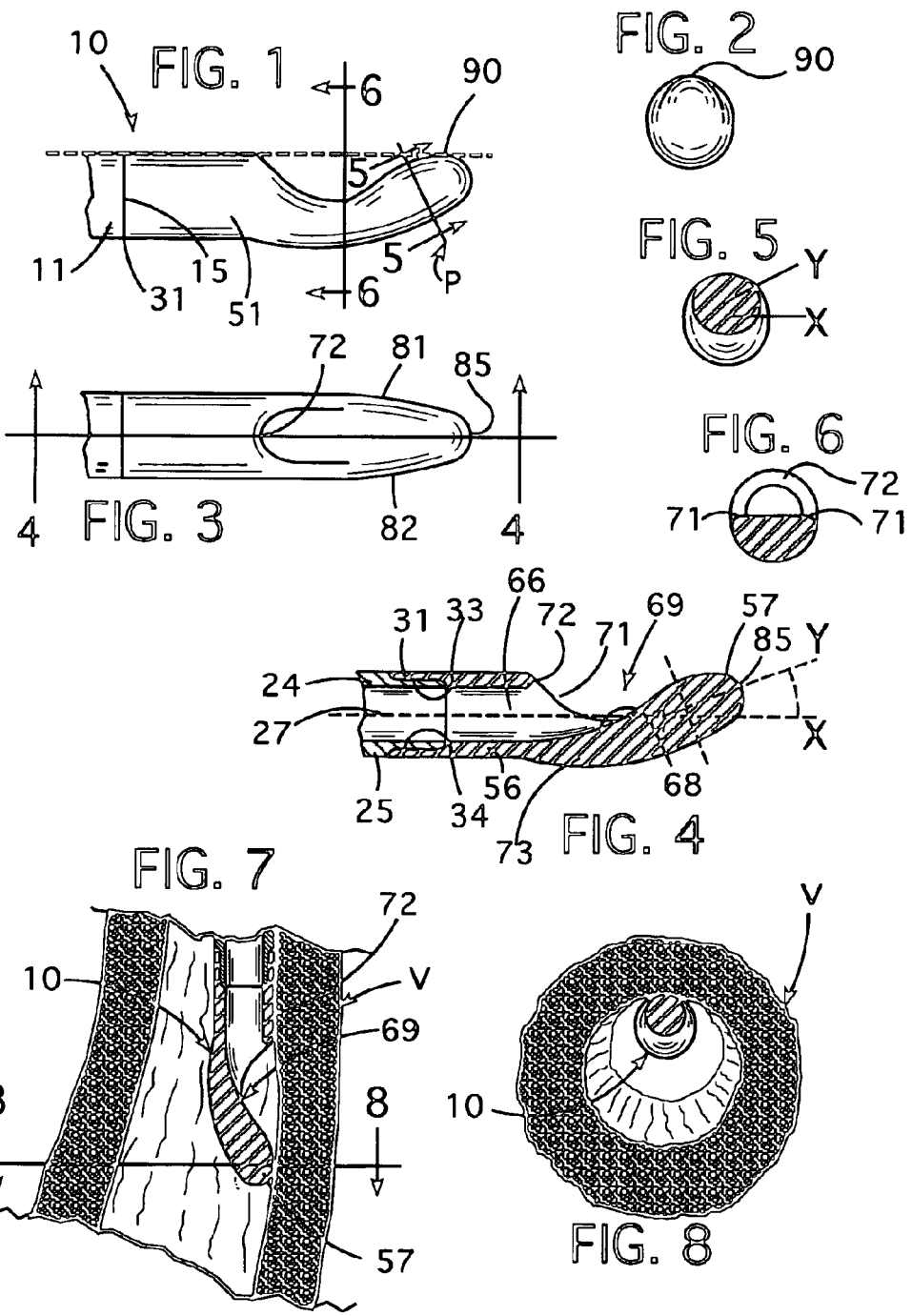

BLOOD VESSEL CATHETER

FIELD OF THE INVENTION

This invention relates in general to medical catheters. It relates, more particularly, to blood vessel catheters.

BACKGROUND OF THE INVENTION

Blood vessel catheters are normally either venous catheters or arterial catheters. Venous catheters, in turn, usually come in several forms. The simplest are short peripheral catheters. Hemodialysis catheters comprise one form of central venous catheter and are normally placed in the superior vena cava.

Blood vessel catheters of almost all types are pliable so that they do not damage body tissue when they are in-situ. Pliability can create a problem during insertion, however, because the catheters can kink when they meet resistance. Thus, there is often a need for a certain amount of stiffness so that the catheters can be directed within body vessels or cavities. There are currently two methods of providing this stiffness; stylets and guide wires.

A stylet can be a single or a twisted wire with a blunt end that is inserted into the catheter to make it stiff. The stylet is often used with bullet nose catheters and maintains its position within the catheter as the catheter is inserted. The stiffened catheter is advanced into the blood vessel with the stylet.

In contrast, guide wires are used to both stiffen the catheter and to provide a guide for the insertion. Commonly, the guide wire is inserted into the blood vessel before the catheter. The catheter is then inserted into the blood vessel over the wire, and follows the wire as it travels inside the vessel. Guide wires are most often utilized with catheters that are inserted deep into the body, such as with central venous catheters that are inserted into the heart. The thin guide wire more easily makes the bends and turns necessary for this type of placement.

In guide wire insertion where the catheter must be inserted over the guide wire, catheters with open ends are normally utilized to permit passage of the guide wire. These catheters are more likely to cause damage to body tissue during insertion than bullet nose catheters, for example, because of their flat ends and side edges. Open ended catheters are also more likely to damage tissue than bullet nose catheters while in-situ. Nevertheless, the need for deep catheter insertion has heretofore made guide wire insertion of open-ended catheters the accepted procedure in spite of the disadvantage of their flat or blunt end design.

As an alternative, bullet nose catheters have been used with guide wires in some applications by incorporating a small hole through the nose for the wire to pass through. This approach has generally been found undesirable, however, because the hole in the bullet nose can later collect particulate matter and be a focal point for infection.

SUMMARY OF THE INVENTION

An object of the present invention is to provide an improved catheter for use with a guidewire.

Another object of the invention is to provide an improved bullet nose bolus for use on catheters ranging in size from 3 French to 22 French in any medical application.

Still another object is to provide a bullet nose bolus for a catheter which is compatible with a guide wire yet does not require an axially extending hole through the nose.

A further object is to provide a bullet nose for a bolus that protects the leading edge of the catheter outflow or inflow port from rubbing against the vessel wall.

Another object is to provide a bullet nose bolus for a catheter that will not kink during insertion.

Another object is to provide a bullet nose bolus for a catheter that can be inserted simultaneously with a guide wire through a flexible introducer sheath that is essentially the same size as the catheter itself.

Another object is to provide a bullet nose bolus for a catheter that follows a guide wire through bends in a patent's vein and turns without causing increased resistance to passage through the vein.

Another object is to provide a bullet nose bolus that always presents a rounded surface to the vein wall, even when the catheter is bending.

Another object is to provide a bolus with a nose which is flexed by the guide wire in only one direction.

The foregoing and other objects are realized in accord with the present invention by providing a blood vessel catheter that combines a single lumen tube and a bolus with a bullet nose. The bolus has an axially elongated side port behind the bullet nose. The bolus is molded of resilient plastic and includes a connector section at its rear end fastened to the distal end of a catheter tube, a nose section with a bullet nose at its front end and a passage section between them. The passage section contains an axially extending passage which communicates with the tube lumen at one end and opens over the base of a radially oriented port at the other end. A longitudinally elongated stiffening arch is formed in the bottom of the bolus passage section, opposite the port.

From approximately the mid-point of the axially elongated port, where the stiffening arch is thickest, the outer surface of the passage section opposite the port begins to curve toward the longitudinal axis of the bolus. At the same point, the opposite side surfaces of the passage section which bracket the port and the arch curve inwardly toward the axis.

The passage section forward of the mid-point of the port, and the nose section, are effectively inclined toward the longitudinal axis of the bolus and the tube. The passage section joins the nose section of the bolus at the forwardmost end of the side port on a transverse plane where the nose section is at a maximum thickness in a direction passing through the bolus axis and the center of the port. The plane is inclined rearwardly toward the port at an angle corresponding to the effective angle of incline of the curving passage section toward the bolus axis. The thickness of the nose section in this plane in the direction of the bolus axis and the port is 25% to 30% less than the outside diameter of the catheter tube.

The nose section of the bolus is thus offset radially to the port side of the longitudinal axis of the bolus. This displacement results in a bolus configuration wherein a portion of the outermost periphery of the nose section is tangent to an imaginary cylinder containing the outer surface of the bolus passage section. This offset nose configuration serves to prevent the trailing edge of the port from abrading the vein wall.

During insertion of the catheter into a patent's vein, however, the offset nose configuration serves another purpose. When a guide wire is passed through the bolus, the nose section flexes toward the longitudinal axis of the bolus to permit the wire to pass without forcing the nose section outside the larger tube profile, i.e., outside the imaginary cylinder in which the outer surface of the passage section lies. This makes insertion of the catheter much easier.

BRIEF DESCRIPTION OF THE DRAWINGS

FIG. 1 is a side elevational view of a blood vessel catheter embodying features of the present invention;

FIG. 2 is a front elevational view of the blood vessel catherer of FIG. 1;

FIG. 3 is top plan view of the blood vessel catheter of FIG. 1;

FIG. 4 is a longitudinal sectional view taken along line 4—4 of FIG. 3;

FIG. 5 is a cross-sectional view taken along line 5—5 of FIG. 1;

FIG. 6 is a cross-sectional view taken along line 6—6 of FIG. 1;

FIG. 7 is a longitudinal sectional view through a patient's vein with the catheter of the invention in-situ, i.e. in a typical operational position in the patient;

FIG. 8 is a cross-sectional view taken along line 8—8 of FIG. 7;

DESCRIPTION OF THE PREFERRED EMBODIMENTS

Figure 9:
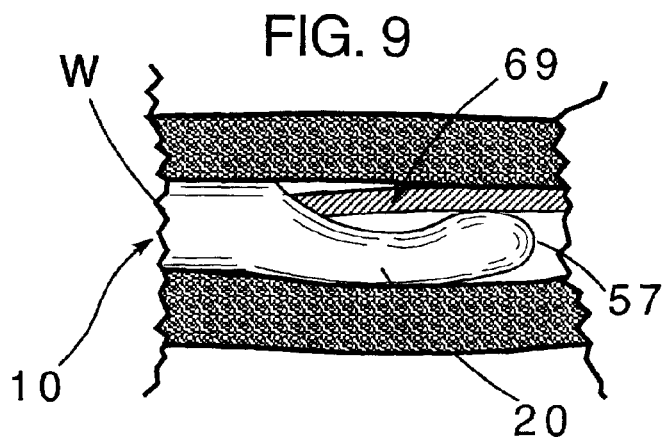
FIG. 9 is a longitudinal sectional view through a patient's vein, with the catheter of the invention in the process of being inserted over a guide wire.

Referring now to the drawings, and particularly to FIGS. 1–3, a blood vessel catheter embodying features of the invention is seen generally at 10. The catheter 10 illustrated here includes a 10.5 French tube 11 which is preferably fabricated from silicone plastic. Although other plastics may be used, including polyurethane, the properties of silicone plastic have been found to be particularly advantageous in the present invention. Specifically, the MED-4770-A & B silicone product manufactured by the NuSil Technologies is preferred.

The 10.5 French catheter tube 11 has a distal end 15. Its proximal end, not shown, will have a conventional connector (not shown) fastened to it. The catheter tube 11 has a bolus 20 fastened to its distal end 15.

Referring additionally to FIGS. 4–6, the 10.5 French catheter tube 11 comprises a tubular plastic body 24 having an outside diameter (O.D.) of 0.136 inches. The body 24 includes a generally cylindrical wall 25 which defines a cylindrical lumen 27 extending through the body, along its entire length.

The distal end 15 of the tube 11 joins the bolus 20 at 31. Forward of the line 31, the tube body 24 has a necked down end 33 which is seated in a suitably formed socket 34 in the bolus 20 and glued or otherwise fastened to the bolus 20. When silicone is used, the components may be welded together for the curing operation.

The bolus 20 comprises a generally cylindrical body 51 molded from silicone. The dimensions of the body 51 vary with the size of the catheter tube 11 in use, but with the 10.5 French tube which is shown here, the body 51 has an O.D. of 0.136 inches. The bolus body 51 comprises a tube connector section 55, a flow passage section 56 and a nose section 57.

The necked down end 33 of the tube body 24 is seated in the socket 34 formed in the connector section 55 of the bolus body 51. The lumen 27 in the tube body 24 communicates with one end of an axially extending passage 66 in the passage section 56 of the bolus body 51. The other end of the axially extending passage 66 opens over a base 68 under a radially oriented port 69. The base 68 curves across the axis X of the bolus body 51 to form the front end of the port 69 opening through the side of the bolus 20.

The port 69 extends around in the passage section 56 to its sides 71, which are low enough to make the port extend circumferentially around about 190° of the body 51, as seen in FIG. 6. The trailing edge 72 of the port 69 is rounded, as seen in FIG. 4, and this rounded edge configuration continues along the top of each side 71 until the side meets the sloping base 68.

Directly opposite the port 69, the passage section 56 below the base 68 is formed outwardly, as at 73, to create a stiffening arch in the bolus body 51. The arch 73 begins opposite the trailing edge 72 of the port, increases in thickness until it is directly under the mid-point of the port 69, and then decreases in thickness toward the nose section 57.

This configuration results in a bolus body 51 wherein the effective axis Y of the passage section 56 in front of the mid-point of the port 69 and the nose section 57 in front of this portion of the passage section is inclined at an angle of 22° to the axis X of the bolus body. The center of the nose section 57 is then offset from the axis X in the radial direction of the port 69.

As best seen in FIG. 3, the outer side surfaces 81 and 82 of the bolus body 51 also taper inwardly beginning approximately at the mid-point of the axially elongated port 69 (at section line 6—6) and converge toward the nose section 57. Each side surface 81 and 82 tapers in an arc to the rounded bullet nose 85 on the nose section 57.

The nose section 57 has a slightly elliptical shape in cross-section on the plane P where it joins the passage section 56, as seen in FIG. 5. The aforedescribed configuration produces a maximum thickness of the nose section 57, in the direction of the port 69 and in the plane P which is 29% smaller than the outside diameter of the catheter tube 11. At the same time, as seen in FIGS. 1 and 2, the outermost periphery of the nose section 57 is, at 90, tangent to an imaginary cylinder defined by the outer surface of the tube 11 and the bolus passage section 56, the cylinder being seen in end view in FIG. 2.

Referring now to FIGS. 7 and 8, a catheter 10 embodying features of the invention is shown in position in a patient's vein V. Here it will be seen that when the position of the catheter 10 in the vein V causes the bolus 20 to be urged against the vein wall where the port 69 emerges, the axially offset nose section 57 engages the wall simultaneously, preventing the trailing edge 72 of the port from abrading the vein wall. In this regard, the segmentally circular cross-sectional configuration of this edge 72 also helps to prevent abrading.

When the catheter 10 is being inserted through a patient's vascular system toward its operational position, it must initially make its way through smaller diameter veins. As seen in FIG. 9, the catheter 10 sometimes must slide through tight quarters in a smaller vein. When insertion is effected over a guide wire W, the configuration of the bolus 20 in the present invention makes this insertion easier and less traumatic for the patient's vascular system, regardless of vein size.

Figure 10:
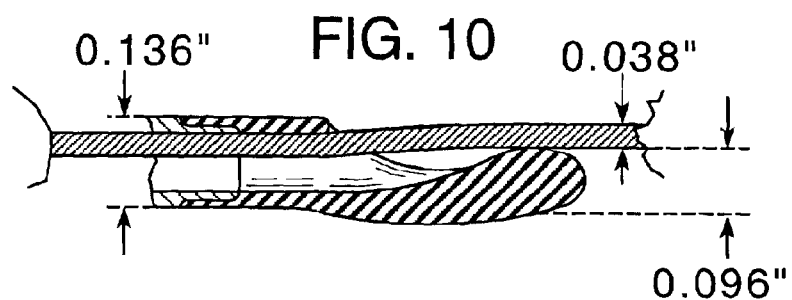
FIG. 10 is a longitudinal sectional view similar to FIG. 4 showing the bolus nose section flexed downwardly by a guide wire.

In FIG. 9, it will be seen that the guide wire W is not forced into the vein wall. Instead, the wire W causes the nose section 57 of the bolus 20 to flex in a plane passing through the axis X of the bolus' passage section and through the center of the port 69. The aforedescribed thickness of the nose section 57 is such that with the nose section flexed to where its axis Y is substantially parallel to the axis X of the bolus body 51, the wire W can pass between the nose section and an undistended vein wall. FIG. 10 illustrates the relative dimensions of catheter 10 and the wire W. Here it will be seen that in the catheter 10 described, the thickness of the flexed nose section 57 is 0.096 inches and the diameter of the wire W is 0.038 inches. Their combined thickness is 0.002 inches less than the diameter of the tube 11.

Figure 11:
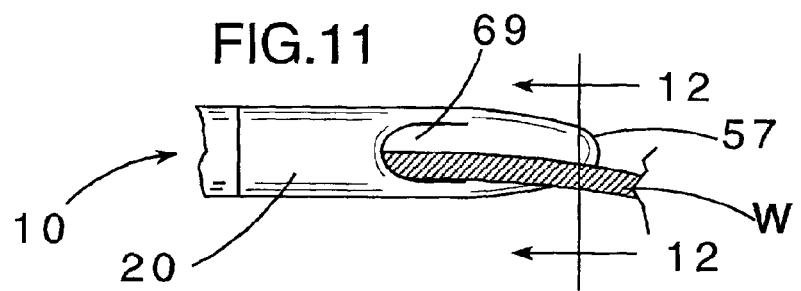
FIG. 11 is a plan view of a catheter bolus and guide wire showing their relative orientation as the catheter is led around a turn in a patient's vein.
Figures 12, 13:
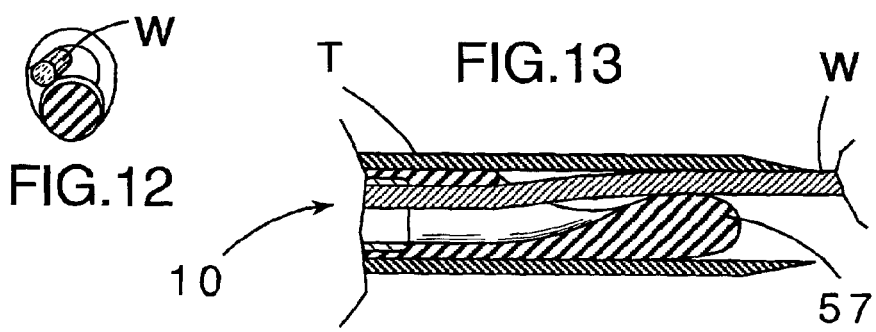
FIG. 12 is a cross-sectional view taken along line 12—12 of FIG. 11.
FIG. 13 is a longitudinal sectional view through an introducer tube with the catheter of the invention in position to be introduced to a vein over a guide wire.

When it is necessary for the bolus 20 and its trailing tube 11 to follow a vein V around turns, the wire W moves off center to one side of the nose section 57, as seen in FIGS. 11 and 12. This sideways movement of the wire W does not force the nose section 57 any substantial distance in the opposite direction, however, because the tapering sides 81 and 82 tend to prevent lateral movement of the bolus 20 at its front end. As a result, the nose section 57 always presents a curved surface to the vein V wall and its rounded bullet nose slides more easily around any turn in a vein.

Turning now to FIG. 13, the catheter 10 of the present invention is illustrated in position inside an introducer tube T as it is prepared for introduction to a patient's vein. Here it will be seen that the shape, size and position of the bolus nose section 57 also permits it to flex easily away from the guide wire W without binding inside the introducer tube T, even though the tube has an O.D. which is only slightly larger than the catheter 10.

The present invention provides the physician with a bullet nose catheter 10 which can be inserted using a guide wire W but which does not require perforation of the bolus nose to facilitate passage of the guide wire. The nose section 57 of the bolus 20 flexes to permit passage of the wire W but, in doing so, does not protrude outside the imaginary cylinder defined by the rest of the bolus and the catheter tube 11, whereby pressure of the bolus on vein V wall is not increased. Nevertheless, with the catheter 10 in operational position in a patient's vein and the wire W removed, the nose section 57 returns to its normal position wherein it prevents the vein wall from wrapping around the bolus port edge 72 and becoming abraded thereby.

While a preferred embodiment of the invention has been described, it should be understood that the invention is not so limited and modifications may be made without departing from the invention. The scope of the invention is defined by the appended claims, and all devices that come within the meaning of the claims, either literally or by equivalence, are intended to be embraced therein.

What is claimed is:

1. A blood vessel-catheter for insertion through a blood vessel, comprising:
   a) a catheter tube and a bolus, said bolus being molded of resilient plastic;
   b) said catheter tube including a body having a cylindrical wall through which a lumen extends to a distal end of the tube;
   c) said bolus including a body having a connector section joined to said catheter tube at said distal end on the longitudinal axis of said tube at its distal end, a passage section and a nose section;
   d) said nose section having a longitudinal axis and an unperforated, rounded bullet nose on its longitudinal axis, said longitudinal axis of said nose section extending through said rounded, bullet nose at its tip;
   e) said passage section of said bolus containing an axially extending passage communicating at one end with said tube lumen and at another end with a port opening radially through the side of said passage section;
   f) said nose section being joined to said passage section at the forward end of said port and in such a manner that the longitudinal axis of said nose section is inclined to one side of the longitudinal axis of said tube at its distal end, said nose section having a maximum thickness on a plane perpendicular to its longitudinal axis which is smaller than the outside diameter of the tube.

2. The catheter of claim 1 further characterized in that:
   a) said port extends around more than 180° of the circumference of said passage section.

3. The blood vessel catheter of claim 1 further characterized in that:
   a) said bolus body has opposite sides bracketing said port which taper radially inwardly as they extend forwardly from said passage section into said nose section.

4. The catheter of claim 1 further characterized in that:
   a) said nose section, where it joins said passage section, has a center which is radially offset from the longitudinal axis of said tube so that a portion of the outer periphery of said bullet nose is substantially tangent with an imaginary cylinder projected forwardly from the cylindrical outer surface of said connector section.

5. The catheter of claim 4 further characterized in that:
   a) said bolus body has opposite sides bracketing said port which taper radially inwardly as they extend forwardly from said passage section into said nose section.

6. The catheter of claim 5 further characterized in that:
   a) said port has a trailing edge at the outer periphery of said passage section;
   b) said radially inward taper of said sides beginning forwardly of said trailing edge.

7. The catheter of claim 4 further characterized in that:
   a) said bolus body includes a longitudinally extending stiffening arch formed outwardly of said passage section opposite said port.

8. A catheter for insertion through a blood vessel, comprising:
   a) a tube having a predetermined outside diameter and a distal end;
   b) a bolus including a connector section, a passage section and a nose section, said connector section having a cylindrical outer surface and being connected to said distal end on a longitudinal axis of said tube at its distal end;
   c) said passage section containing an axially extending passage and a radially extending port which opens through the side of said bolus behind said nose section;
   d) said nose section being joined to said passage section at the forward end of said passage section and having a bullet nose, the maximum cross-sectional diameter of said nose section where it joins said passage section being substantially less than said predetermined diameter;

e) said nose section having a longitudinal axis which extends through the tip of a bullet nose on said nose section and which is inclined from said longitudinal axis of said tube, and said bullet nose having a rounded external surface portion which is substantially tangent to an imaginary cylinder projected forwardly from the cylindrical outer surface of said connector section.

9. The catheter of claim 8 further characterized in that:

a) said maximum outside diameter of said nose section where it joins said passage section being at least 25 percent smaller than the maximum diameter of said passage section.

10. The catheter of claim 9 further characterized in that:

a) said bolus body includes a longitudinally extending stiffening arch formed radially outwardly of said passage section opposite said port;

b) said stiffening arch having an outer surface which defines an arc extending the length of said port and contiguous with the outer surface of the bullet nose.

11. The catheter of claim 7 or 8 further characterized in that:

a) said stiffening arch having an outer surface which defines an arc extending the length of said port and contiguous with the outer surface of the bullet nose.

12. A blood vessel catheter, comprising:

a) a catheter tube and a bolus, said bolus being molded of resilient plastic;

b) said catheter tube including a body having a cylindrical wall through which a lumen extends to an opening at the distal end of the tube;

c) said bolus including a body having a connector section joined to said catheter tube at said distal end, and a nose section;

d) said nose section having a longitudinal axis and an unperforated, rounded bullet nose on its longitudinal axis, said longitudinal axis of said nose section extending through said rounded, bullet nose at its tip;

e) said bolus nose section being positioned in front of said lumen opening and forming a port opening radially from the side of said catheter;

f) the longitudinal axis of said nose section being inclined to one side of the longitudinal axis of said tube at its distal end, said nose section having a maximum thickness on a plane perpendicular to its longitudinal axis which is smaller than the outside diameter of the tube.

13. The catheter of claim 12 further characterized in that:

a) said nose section has a center which is radially offset from the longitudinal axis of said tube so that a portion of the outer periphery of said bullet nose is substantially tangent with an imaginary cylinder projected forwardly from the cylindrical outer surface of said tube.

14. The catheter of claim 12 or 13 further characterized in that:

a) said bolus body includes a longitudinally extending stiffening arch formed radially outwardly of said passage section opposite said port;

b) said stiffening arch having an outer surface which defines an arc extending the length of said port and contiguous with the outer surface of the bullet nose;

c) the resulting shape of said nose section being arcuate and curving in the radial direction of said port to its bullet nose tip.

15. The catheter of claim 14 further characterized in that:

a) said catheter, including said radially outwardly extending arch, has a maximum cross-sectional area along its length from the catheter tube to the tip of said bolus which never exceeds that of the cross-sectioned area of the tube.

\* \* \* \* \*